United States Patent
Govari et al.

(10) Patent No.: US 11,712,287 B2
(45) Date of Patent: Aug. 1, 2023

(54) GRASPER TOOL WITH COAGULATION

(71) Applicant: BIOSENSE WEBSTER (ISRAEL) LTD., Yokneam (IL)

(72) Inventors: Assaf Govari, Haifa (IL); Yehuda Algawi, Binyamina (IL); Vadim Gliner, Yokneam (IL); Ilya Sitnitsky, Nahariya (IL); Andres Claudio Altmann, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 253 days.

(21) Appl. No.: 16/797,586

(22) Filed: Feb. 21, 2020

(65) Prior Publication Data

US 2020/0330150 A1 Oct. 22, 2020

Related U.S. Application Data

(60) Provisional application No. 62/835,916, filed on Apr. 18, 2019.

(51) Int. Cl.
*A61B 18/14* (2006.01)
*A61B 34/20* (2016.01)
(Continued)

(52) U.S. Cl.
CPC ............ *A61B 18/1445* (2013.01); *A61B 2018/00023* (2013.01); *A61B 2018/00107* (2013.01);
(Continued)

(58) Field of Classification Search
CPC .......... A61B 2018/00928; A61B 2018/00666; A61B 2018/00589; A61B 90/06;
(Continued)

(56) References Cited

U.S. PATENT DOCUMENTS 3,100,489 A * 8/1963 Bagley ............... A61B 18/1442
606/42
4,492,231 A * 1/1985 Auth .................. A61B 18/1442
606/42
(Continued)

FOREIGN PATENT DOCUMENTS

EP 0913126 10/2004
EP 3120793 1/2017

OTHER PUBLICATIONS

European Search Report dated Sep. 23, 2020 from corresponding European Patent Application No. 20170012.7-1115.

*Primary Examiner* — Khadijeh A Vahdat
*Assistant Examiner* — Marina Delaney Templeton
(74) *Attorney, Agent, or Firm* — Frost Brown Todd LLP

(57) ABSTRACT

In one embodiment, a medical system includes a medical instrument having a grasper head including first and second complementary grasping jaws, and first and second conducting surfaces disposed on respective distal portions of the first and second grasping jaws, the conducting surfaces being electrically isolated from each other in the grasper head, an actuator configured to close the grasping jaws so as to bring the conducting surfaces into contact with a tissue of a body part of a living subject, and a proximity sensor configured to output at least one proximity signal responsive to a displacement between the grasping jaws, and processing circuitry coupled to sense the displacement between the first and second grasping jaws responsively to the at least one proximity signal, and apply an electrical current between the first and second conducting surfaces of the grasping jaws when the sensed displacement is less than a given threshold displacement.

20 Claims, 9 Drawing Sheets

(51) Int. Cl.
 *A61B 34/30* (2016.01)
 *A61B 18/00* (2006.01)
 *A61B 18/12* (2006.01)
(52) U.S. Cl.
 CPC ........... *A61B 2018/00327* (2013.01); *A61B 2018/00446* (2013.01); *A61B 2018/00589* (2013.01); *A61B 2018/1266* (2013.01); *A61B 2034/2063* (2016.02); *A61B 2034/303* (2016.02); *A61B 2218/002* (2013.01)
(58) Field of Classification Search
 CPC ...... A61B 2034/2051; A61B 2218/002; A61B 18/12; A61B 18/1445; A61B 18/1442; A61B 2017/2845; A61B 17/282; A61B 17/29; A61B 17/320092; A61M 2025/0002; A63B 2220/83; A63F 2003/00671
 See application file for complete search history.

(56) References Cited

U.S. PATENT DOCUMENTS

| | | | |
|---|---|---|---|
| 5,456,684 A | 10/1995 | Schmidt et al. | |
| 5,810,809 A | 9/1998 | Rydell | |
| 6,235,027 B1* | 5/2001 | Herzon | A61B 18/08 606/49 |
| 7,491,202 B2* | 2/2009 | Odom | A61B 18/1445 606/51 |
| 8,262,655 B2* | 9/2012 | Ghabrial | A61B 18/1445 606/51 |
| 8,702,702 B1 | 4/2014 | Edwards et al. | |
| 11,419,665 B2* | 8/2022 | Mercier | A61B 18/1442 |
| 2007/0005061 A1* | 1/2007 | Eder | A61B 18/1442 606/51 |
| 2008/0009860 A1* | 1/2008 | Odom | A61B 18/1445 606/51 |
| 2008/0195093 A1* | 8/2008 | Couture | A61B 18/1445 606/45 |
| 2008/0215048 A1* | 9/2008 | Hafner | A61B 18/1442 606/42 |
| 2009/0261804 A1* | 10/2009 | McKenna | A61B 18/1447 324/71.1 |
| 2010/0076427 A1* | 3/2010 | Heard | A61B 18/1233 606/45 |
| 2011/0092970 A1* | 4/2011 | Alberstetter | A61B 18/1442 606/41 |
| 2011/0098689 A1* | 4/2011 | Nau, Jr. | A61B 17/320092 606/205 |
| 2013/0338660 A1* | 12/2013 | Rothweiler | A61B 18/18 606/33 |
| 2014/0094788 A1* | 4/2014 | Brannan | A61B 18/1233 606/34 |
| 2014/0148729 A1 | 5/2014 | Schmitz et al. | |
| 2015/0112338 A1 | 4/2015 | Unger et al. | |
| 2016/0007842 A1 | 1/2016 | Govari et al. | |
| 2016/0074103 A1* | 3/2016 | Sartor | A61B 18/1445 606/51 |
| 2016/0270840 A1* | 9/2016 | Yates | A61B 18/1445 |
| 2017/0020601 A1* | 1/2017 | Thomson | A61B 17/3201 |
| 2017/0105786 A1* | 4/2017 | Scheib | A61B 18/1442 |
| 2017/0325878 A1* | 11/2017 | Messerly | A61B 18/1445 |
| 2018/0360445 A1* | 12/2018 | Shelton, IV | A61B 17/07207 |

* cited by examiner

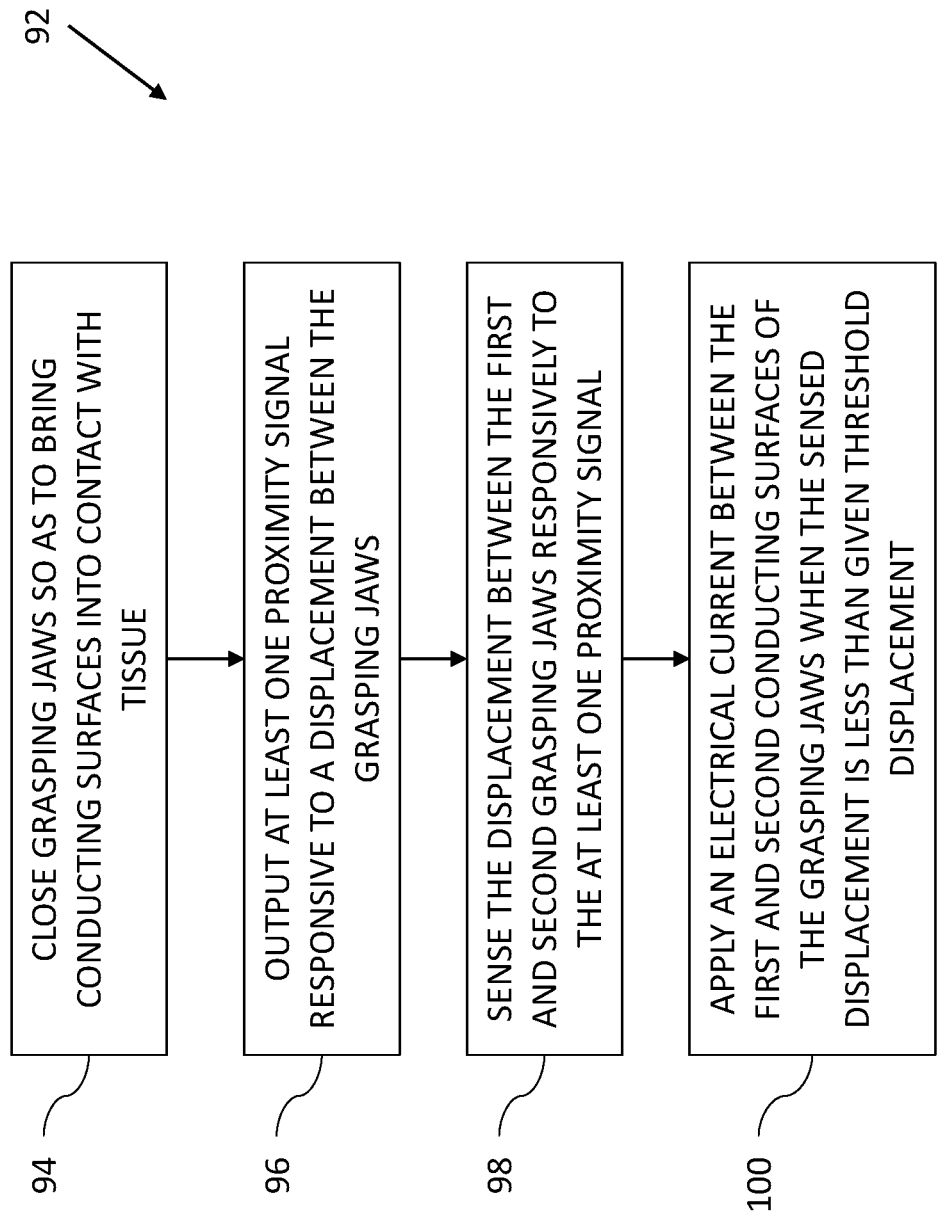

GRASPER TOOL WITH COAGULATION

RELATED APPLICATION INFORMATION

The present application claims benefit of U.S. Provisional Patent Application No. 62/835,916 of Govari, et al., filed on Apr. 18, 2019.

FIELD OF THE INVENTION

The present invention relates to medical tools, and in particular, but not exclusively, to grasper tools.

BACKGROUND

Graspers may be used in medical applications to grasp, and remove and/or cut tissue, which generally results in massive bleeding. Coagulation in surgical procedures may be performed by applying an electrical current to the bleeding tissue.

By way of example, U.S. Pat. No. 5,810,809 to Rydell describes an arthroscopy instrument for debriding tissue which includes an electrocautery electrode for effecting hemostasis in a surgical site. A drive motor for the debriding instrument is placed remotely from the instrument's handle and provision is made for electrically insulating the handle from the drive motor and associated power supply even though the arthroscopic surgery is taking place under saline.

U.S. Pat. No. 8,702,702 to Edwards, et al., describes a mechanical cutting device that makes use of mechanical (rotary) motion and suction to engage tissue and also applies a cutting energy sufficient to vaporize the tissue. The rotation and suction are used to engage the tissue (sucking tissue into cutting windows when the cutting windows of inner and outer blades are aligned), and then the cutting member(s) function as an electrode(s) by having an electrical cutting signal applied thereto so that the cutting member(s) electrically cut the tissue as the cutting members relatively rotate. The electrical cutting signal is only applied as the windows become aligned up until the cutting of the tissue is completed. The cutting signal preferably is stopped after the cutting windows become misaligned. While the cutting windows are misaligned, a coagulation signal can be supplied to the cutting member so that the device functions as an electrocautery device.

US Patent Publication 2014/0148729 of Schmitz, et al., now abandoned, describes a method for removing at least part of a brain tumor and may first involve contacting a forward-facing tissue cutter disposed at the distal end of a tissue removal device with the brain tumor. The tissue removal device may include a shaft having a diameter no greater than about 10 mm, and in some embodiments the tissue cutter does not extend laterally beyond the diameter of the shaft. The method may next involve cutting tissue from the brain tumor, using the tissue cutter. The method may then involve moving the cut tissue through a channel of the shaft in a direction from the distal end of the tissue removal device toward a proximal end of the device.

European Patent Publication EP0913126 of Kese, et al., describes open surgery and endoscopic versions of a combined bipolar electrosurgical cutting and grasping instrument where the grasping surfaces are contained within the shape of a standard surgical scissor. This unique arrangement results in a combined scissor and grasper which has the feel of a standard scissor but which allows surgeons to cauterize tissue and vessels while both cutting and grasping thus making the instruments well suited to perform coaptation of vessels.

SUMMARY

There is provided in accordance with an embodiment of the present disclosure, a medical system, including a medical instrument including a grasper head including first and second complementary grasping jaws, and first and second conducting surfaces disposed on respective distal portions of the first and second grasping jaws, the first and second conducting surfaces being electrically isolated from each other in the grasper head, an actuator configured to close the grasping jaws so as to bring the first and second conducting surface into contact with a tissue of a body part of a living subject, and a proximity sensor configured to output at least one proximity signal responsive to a displacement between the first and second grasping jaws, and processing circuitry coupled to sense the displacement between the first and second grasping jaws responsively to the at least one proximity signal, and apply an electrical current between the first and second conducting surfaces of the grasping jaws when the sensed displacement is less than a given threshold displacement.

Further in accordance with an embodiment of the present disclosure the proximity sensor includes two electrical contacts disposed on the grasper head and configured to make mutual contact with each other when the displacement between the first and second grasping jaws is less than the given threshold displacement.

Still further in accordance with an embodiment of the present disclosure respective ones of the electrical contacts are connected to the grasper head via respective springs.

Additionally, in accordance with an embodiment of the present disclosure the grasper head includes at least one position tracking transducer configured to provide a position signal indicative of a position of the grasper head, and the processing circuitry being configured to compute a position of the grasper head responsively to the position signal.

Moreover in accordance with an embodiment of the present disclosure the proximity sensor includes two position tracking transducers disposed in the grasper head and configured to provide respective position signals, included in the at least one proximity signal, indicative of respective positions of the first and second grasping jaws, and the processing circuitry being configured to compute the displacement between the first and second grasping jaws responsively to the respective position signals.

Further in accordance with an embodiment of the present disclosure, the system includes an irrigation pump, wherein the medical instrument includes an irrigation tube coupled to the irrigation pump, the irrigation pump being configured to pump a fluid into the irrigation tube to cool the tissue.

Still further in accordance with an embodiment of the present disclosure the grasper head includes two elongated members including the first and second grasping jaws, and a pin connecting the two elongated members to allow angular motion between the first and second grasping jaws.

Additionally, in accordance with an embodiment of the present disclosure the proximity sensor includes two electrical contacts disposed on two opposing sides of the two elongated members and configured to make mutual contact with each other when the displacement between the first and second grasping jaws is less than the given threshold displacement.

Moreover, in accordance with an embodiment of the present disclosure respective ones of the electrical contacts are connected to the elongated members via respective springs.

There is also provided in accordance with another embodiment of the present disclosure a medical method, including closing first and second grasping jaws of a grasper head of a medical instrument so as to bring first and second conducting surfaces disposed on respective distal portions of the first and second grasping jaws into contact with a tissue of a body part of a living subject, the first and second conducting surfaces being electrically isolated from each other in the grasper head, outputting at least one proximity signal responsive to a displacement between the first and second grasping jaws, sensing the displacement between the first and second grasping jaws responsively to the at least one proximity signal, and applying an electrical current between the first and second conducting surfaces of the grasping jaws when the sensed displacement is less than a given threshold displacement.

Further in accordance with an embodiment of the present disclosure, the method includes two electrical contacts making mutual contact with each other when the displacement between the first and second grasping jaws is less than the given threshold displacement.

Still further in accordance with an embodiment of the present disclosure respective ones of the electrical contacts are connected to the grasper head via respective springs.

Additionally, in accordance with an embodiment of the present disclosure, the method includes providing a position signal indicative of a position of the grasper head, and computing a position of the grasper head responsively to the position signal.

Moreover in accordance with an embodiment of the present disclosure, the method includes two position tracking transducers disposed in the grasper head providing respective position signals, included in the at least one proximity signal, indicative of respective positions of the first and second grasping jaws, and computing the displacement between the first and second grasping jaws responsively to the respective position signals.

Further in accordance with an embodiment of the present disclosure, the method includes pumping a fluid into an irrigation tube of the medical instrument to cool the tissue.

BRIEF DESCRIPTION OF THE DRAWINGS

The present invention will be understood from the following detailed description, taken in conjunction with the drawings in which:

FIG. 9 is a flowchart including exemplary steps in a method of operation of the system of FIG. 1.

DESCRIPTION OF EXAMPLE EMBODIMENTS

Overview

Figure 1:
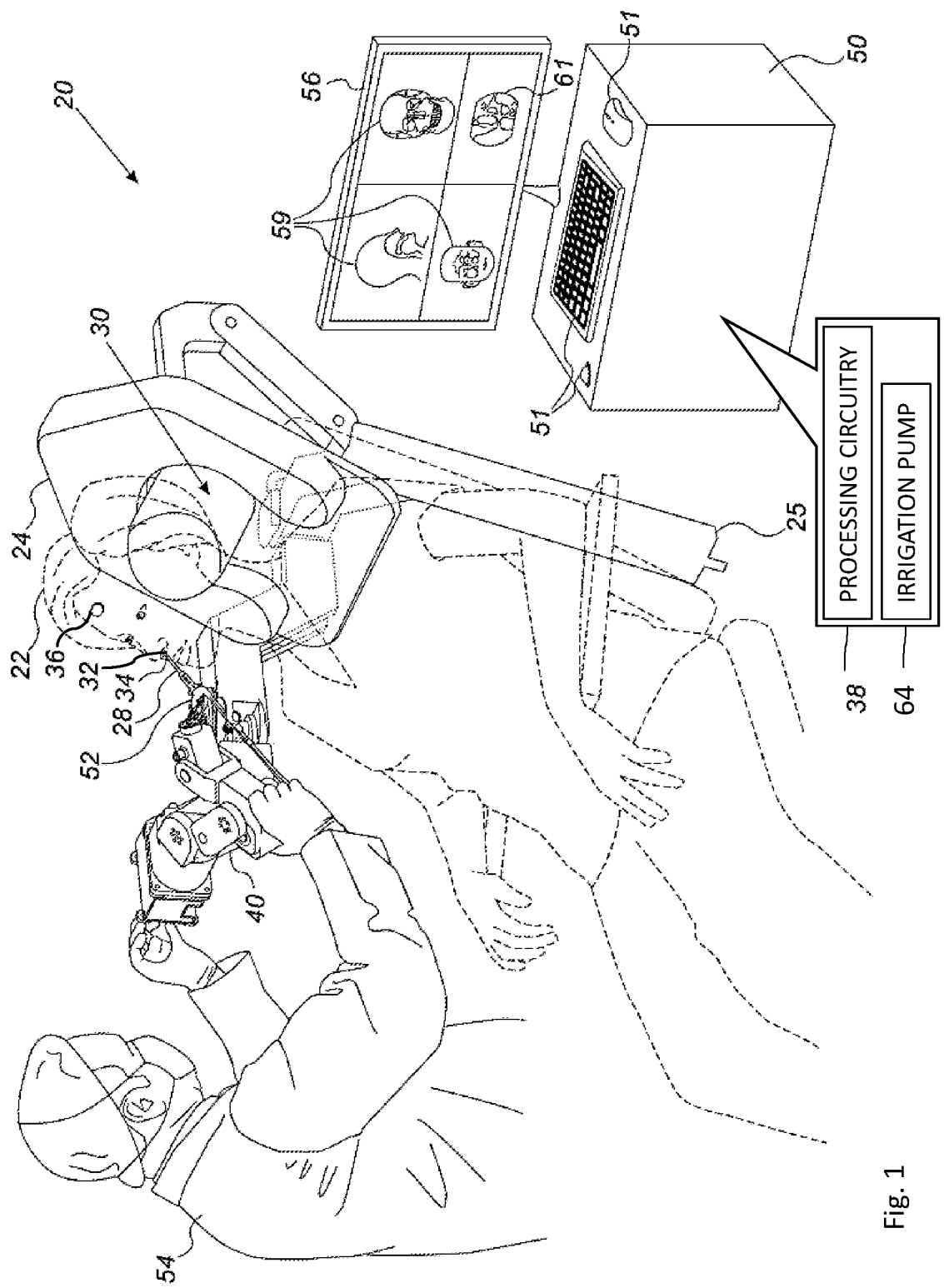
FIG. 1 is a schematic illustration of a medical procedure system, according to an embodiment of the present invention.

As mentioned above, graspers may be used in medical applications to grasp, and remove and/or cut tissue, which generally results in massive bleeding. Coagulation in surgical procedures may be performed by applying an electrical current to the bleeding tissue.

Performing coagulation with a medical instrument may be complicated by the geometry and mechanical structure of the medical instrument. For example, if a medical instrument includes many conducting surfaces, applying an electrical current may be limited due to inherent short circuits caused by the metal surfaces.

Embodiments of the present invention include a system comprising a medical instrument to grasp tissue and automatically apply an electrical current to the grasped tissue in response to the tissue being grasped thereby performing coagulation at the time the tissue is likely to be bleeding. The electrical current is automatically applied in response to grasping the tissue based on sensing a displacement between complementary grasping jaws of a grasper head of the medical instrument. Automatically applying the electrical current prevents the physician from forgetting to perform coagulation each time the tissue is grasped, and also allows the physician to concentrate on other tasks at hand.

The grasping jaws include conducting surfaces through which to apply the electrical current to the tissue. The conducting surfaces are electrically connected to processing circuitry, but the conducting surfaces are electrically isolated from each other in the grasper head. This electrical isolation may be implemented by forming at least part of the grasper head or at least part of the grasping jaws from an insulating material, such as a biocompatible plastic. In some embodiments, the grasper head and or grasping jaws may be formed from a conducting material which is coated with an insulating material, such as biocompatible plastic.

In some embodiments, the grasper head comprises two elongated members including the grasping jaws, and a pin connecting the two elongated members allowing angular motion between the grasping jaws.

The medical instrument includes an actuator to close the grasping jaws so as to bring the conducting surfaces into contact with a tissue of a body part of a living subject.

The grasper head also includes at least one position tracking transducer providing a position signal indicative of a position of the grasper head. Processing circuitry computes a position of the grasper head responsively to the position signal. A representation of the grasper head in a body part may be rendered to a display screen based on the computed position. A physician may then navigate the grasper head within the body part according to the rendered representation of the grasper head.

The grasper head includes a proximity sensor which outputs one or more proximity signals responsive to a displacement between the grasping jaws.

In some embodiments, the proximity sensor includes two electrical contacts disposed on the grasper head. The electrical contacts make mutual contact with each other when the displacement between the grasping jaws is less than a given threshold displacement, which for example is around 2 mm or in the range of 1-4 mm. The electrical contacts may be connected to the grasper head via respective springs.

In some embodiments, the proximity sensor includes two electrical contacts disposed on two opposing sides of the two elongated members. The electrical contacts make mutual contact with each other when the displacement between the grasping jaws is less than the given threshold displacement. The electrical contacts may be connected to the elongated members via respective springs.

In some embodiments, the proximity sensor includes two position tracking transducers disposed in the grasper head. The position tracking transducers provide position signals indicative of positions of the grasping jaws. The processing circuitry computes the displacement between the grasping jaws responsively to the position signals.

The processing circuitry is coupled to sense the displacement between the grasping jaws responsively to the proximity signal(s). Sensing the displacement may be based on the two electrical contracts making mutual contact. Alternatively, sensing the displacement may be performed by computing the displacement between the grasping jaws.

The processing circuitry applies an electrical current between the conducting surfaces of the grasping jaws when the sensed displacement is less than a given threshold displacement. The processing circuitry may apply the electrical current between the conducting surfaces as a result of the two electrical contacts making mutual contact and thereby closing a circuit resulting in the flow of the electrical current. Alternatively, the processing circuitry may apply the electrical current in response to the computed displacement being less than the given threshold displacement.

The system may also include an irrigation pump and an irrigation tube, which is disposed in the medical instrument. The irrigation tube is coupled to the irrigation pump. The irrigation pump pumps a fluid into the irrigation tube to cool the tissue, which has been heated by the applied electrical current.

System Description

Figure 2:
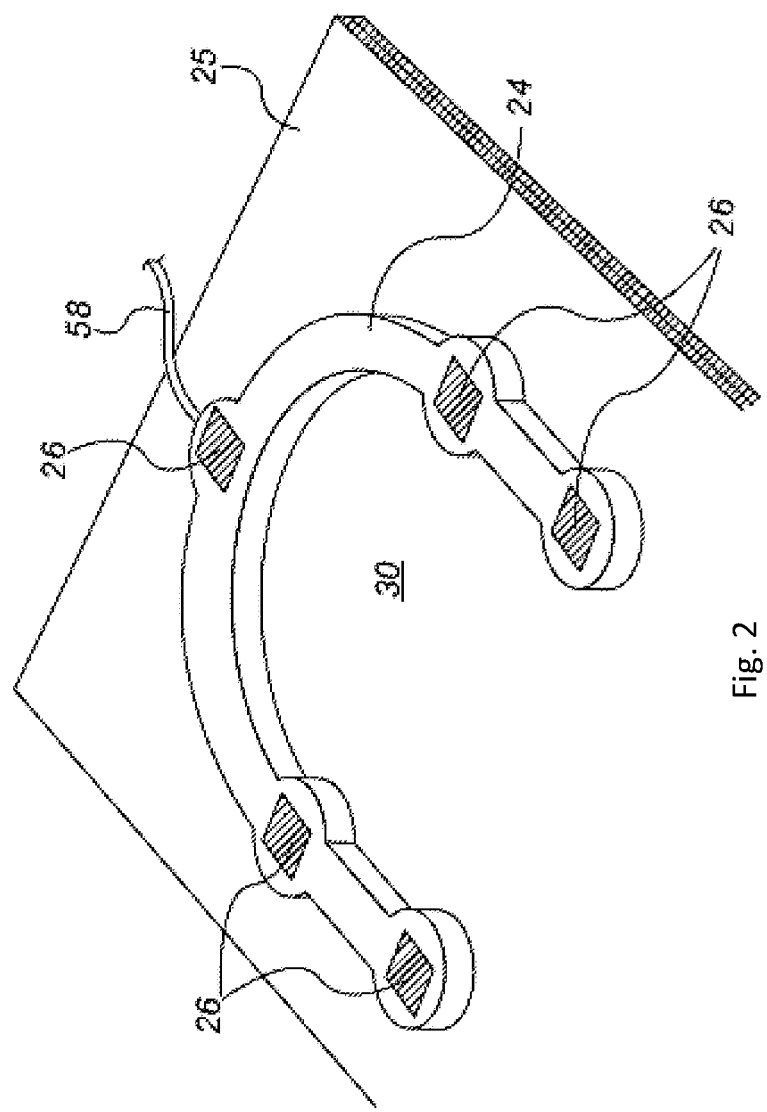
FIG. 2 is a schematic illustration of a magnetic field radiation assembly used in the medical procedure system, according to an embodiment of the present invention.

Turning now to the drawings, reference is now made to FIG. 1, which is a schematic illustration of a medical procedure system 20, and to FIG. 2, which is a schematic illustration of a magnetic field radiation assembly location pad 24 used in the system 20, according to an embodiment of the present invention. The medical procedure system 20 is typically used during an invasive and/or investigative procedure on a nasal sinus or another body part (such as the brain) of a patient 22.

For the procedure, the magnetic field radiation assembly 24 may be positioned behind and/or around the head of the patient 22, for example by fixing the assembly 24 to a chair 25 (or bed) upon which the patient is sitting (or lying). The magnetic field radiation assembly 24 in the pictured example comprises five magnetic field radiators 26, which are fixed in a horseshoe shaped frame, the frame being positioned beneath or around the patient 22 so that the magnetic field radiators 26 surround the head of the patient 22. Alternatively, smaller or larger numbers of radiators 26 may be used, in various different configurations. The magnetic field radiators 26 are configured to radiate alternating magnetic fields at respective frequencies into a region 30 where the body part is located, in proximity to the magnetic field radiation assembly 24 and which includes the head of patient 22.

The alternating magnetic fields induce signals in a position-tracking transducer 32 and a position-tracking transducer 36. The position-tracking transducer 32 is shown disposed on a medical instrument 28 in order to track a position of the medical instrument 28. The position-tracking transducer 36 is shown disposed on the patient 22 (e.g., on the forehead of the patient 22 or any other suitable body part) in order to track a position of the patient 22 (e.g., to track a position of the head of the patient 22) to compensate for movement of the patient with respect to the magnetic field radiation assembly 24. By way of example only, the medical instrument 28 may include any one or more of the following, a probe for inserting into the body-part, an endoscope, and/or a surgical tool such as an ENT tool, suction tool, microdebrider, shaver, and/or grasper.

The position of the distal end of the medical instrument 28 and the position of the patient 22, may be tracked using a tracking subsystem, which tracks position and orientation coordinates of the position-tracking transducer 32 fitted at the distal end and the position-tracking transducer 36, respectively. The position-tracking transducers 32, 36 are configured to output signals that are indicative of locations of the transducers 32, 36, respectively. The signals are processed by the tracking subsystem running on processing circuitry 38 to track the locations of the distal end of the medical instrument 28 and the position of the patient 22 over time. In embodiments, where the tracking subsystem is a magnetic tracking subsystem, the position-tracking transducer 32 and/or the position-tracking transducer 36 includes at least one coil, and typically two or three orthogonally placed coils. In other embodiments, the tracking subsystem may be an electrically-based tracking subsystem using multiple head surface electrodes (e.g., multiple instances of the position-tracking transducer 36) to track the position of the medical instrument 28 based on a signal emitted by at least one electrode (comprised in the position-tracking transducer 32) of the medical instrument 28. The tracking subsystem may be implemented using any suitable location tracking subsystem, for example, but not limited to, an ultrasound-based tracking system where the position-tracking transducer 32 includes at least one ultrasound transducer. Using tracking subsystem, a physician 54 advances the distal end of the medical instrument 28 in a body-part, described in more detail below.

In some embodiments, the medical instrument 28 is attached to, and held by, a robotic arm 40, which is configured to manipulate the medical instrument 28. The robotic arm 40 includes a plurality of robotic joints configured to control movement of the robotic arm 40 and manipulate the medical instrument 28. In other embodiments, the medical instrument 28 is held and manipulated by the physician 54.

As described in more detail below, position-tracking transducer 32 is affixed to the medical instrument 28, and determination of the location and orientation of the position-tracking transducer 32 enables tracking the location and orientation of a distal end 34 (or other location) of the medical instrument 28, that may be reversibly inserted into a body-part of the patient 22 (the living subject).

Similarly, determination of the location and orientation of the position-tracking transducer 36 enables the location and orientation of a part (e.g., the head) of the patient 22 to be tracked. The position-tracking transducer 36 is shown in FIG. 1 as being disposed on the forehead of the patient 22. The position-tracking transducer 36 may be disposed on any other suitable body part of the patient 22 in order to track the position/movement of the patient 22.

A system using magnetic field radiators, such as the magnetic field radiators 26, for tracking an entity inserted into a patient is described in US Patent Publication 2016/0007842, of Govari et al., issued as U.S. Pat. No. 10,772,489 on Sep. 15, 2020. In addition, the Carto® system produced by Biosense Webster of 33 Technology Drive, Irvine, Calif. 92618 USA, uses a tracking system similar to that described herein for finding the location and orientation of a coil in a region irradiated by magnetic fields.

The robotic arm 40 generally has its own robotic coordinate system. The robotic coordinate system is registered with a magnetic coordinate system of the magnetic field radiators 26 or vice-versa. Registration of the robotic coordinate system with the magnetic coordinate system may be performed, for example, by moving the robotic arm 40, or the medical instrument 28 attached to the robotic arm 40, to one or more locations known to the magnetic field radiators 26, for example, to a location on the magnetic field radiation assembly 24 or to the position-tracking transducer 36 or to one or more other known locations on the patient 22. Once registration of the robotic coordinate system with the magnetic coordinate system has been performed, locations in the magnetic coordinate system can be translated to the robotic coordinate system in order to manipulate the robotic arm 40 correctly.

Elements of system 20, including radiators 26, may be controlled by the processing circuitry 38, which comprises a processing unit communicating with one or more memories. Typically, the elements may be connected by cables to the processing circuitry 38, for example, radiators 26 may be connected by a cable 58 to the processing circuitry 38. Alternatively, or additionally, the elements may be coupled wirelessly to the processing circuitry 38. The processing circuitry 38 may be mounted in a console 50, which comprises operating controls 51 that typically include a keypad and/or a pointing device such as a mouse or trackball. The console 50 also connects to other elements of the medical procedure system 20, such as a proximal end 52 of the medical instrument 28. A physician 54 uses the operating controls 51 to interact with the processing circuitry 38 while performing the procedure, and the processing circuitry 38 may present results produced by system 20 on a display 56.

In some embodiments, prior to performing the medical procedure, CT images of the patient 22 are acquired. The CT images are stored in a memory (not shown) for subsequent retrieval by the processing circuitry 38. In FIG. 1, the display 56 is shown displaying various views 59 of a previous CT scan (or other suitable scan) which may be used as an aid for the physician 54 to guide the medical instrument 28 in the body-part. The display screen 56 also shows an image 61 captured by a camera (not shown) of the medical instrument 28. The CT images may be registered with the magnetic coordinate system so that a representation of the medical instrument 28 may be displayed with the CT images on the display 56.

In practice, some or all of these functions of the processing circuitry 38 may be combined in a single physical component or, alternatively, implemented using multiple physical components. These physical components may comprise hard-wired or programmable devices, or a combination of the two. In some embodiments, at least some of the functions of the processing circuitry may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

The system 20 may also include an irrigation pump 64 disposed in the console 50. The irrigation pump 64 is described in more detail with reference to FIGS. 3-6.

Figure 3:
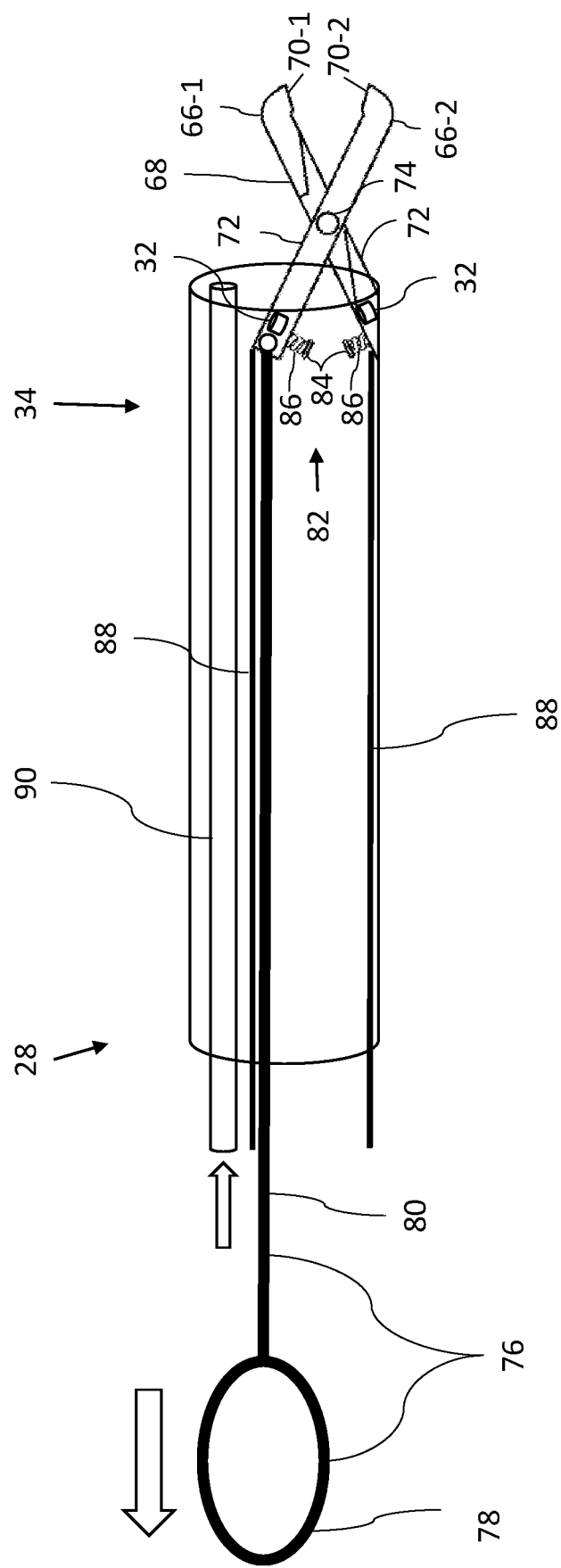
FIG. 3 is a schematic illustration of a medical instrument according to an embodiment of the present invention.
Figure 4:
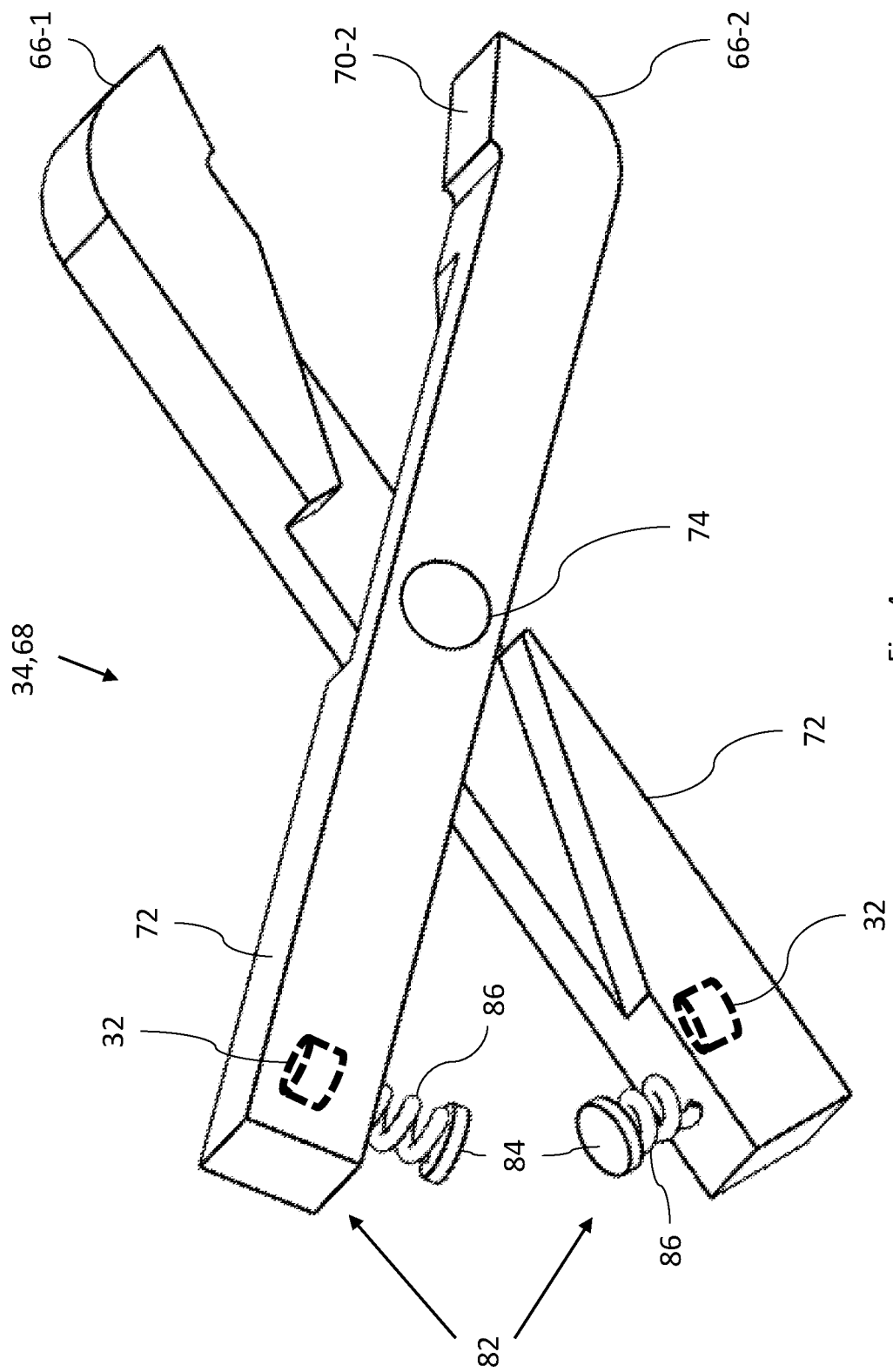
FIGS. 4-6 are various schematic views of the distal end of the medical instrument of FIG. 3.
Figure 5:
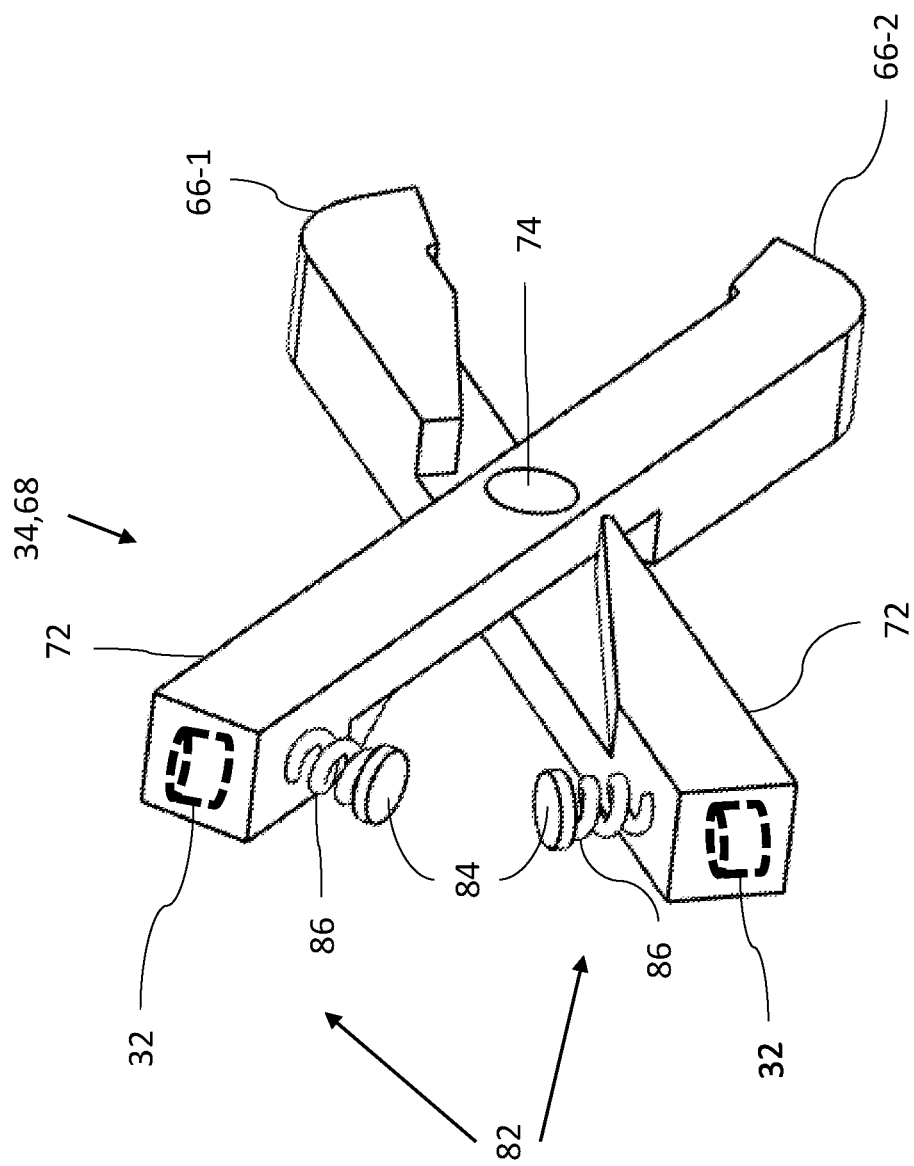
Figure 6:
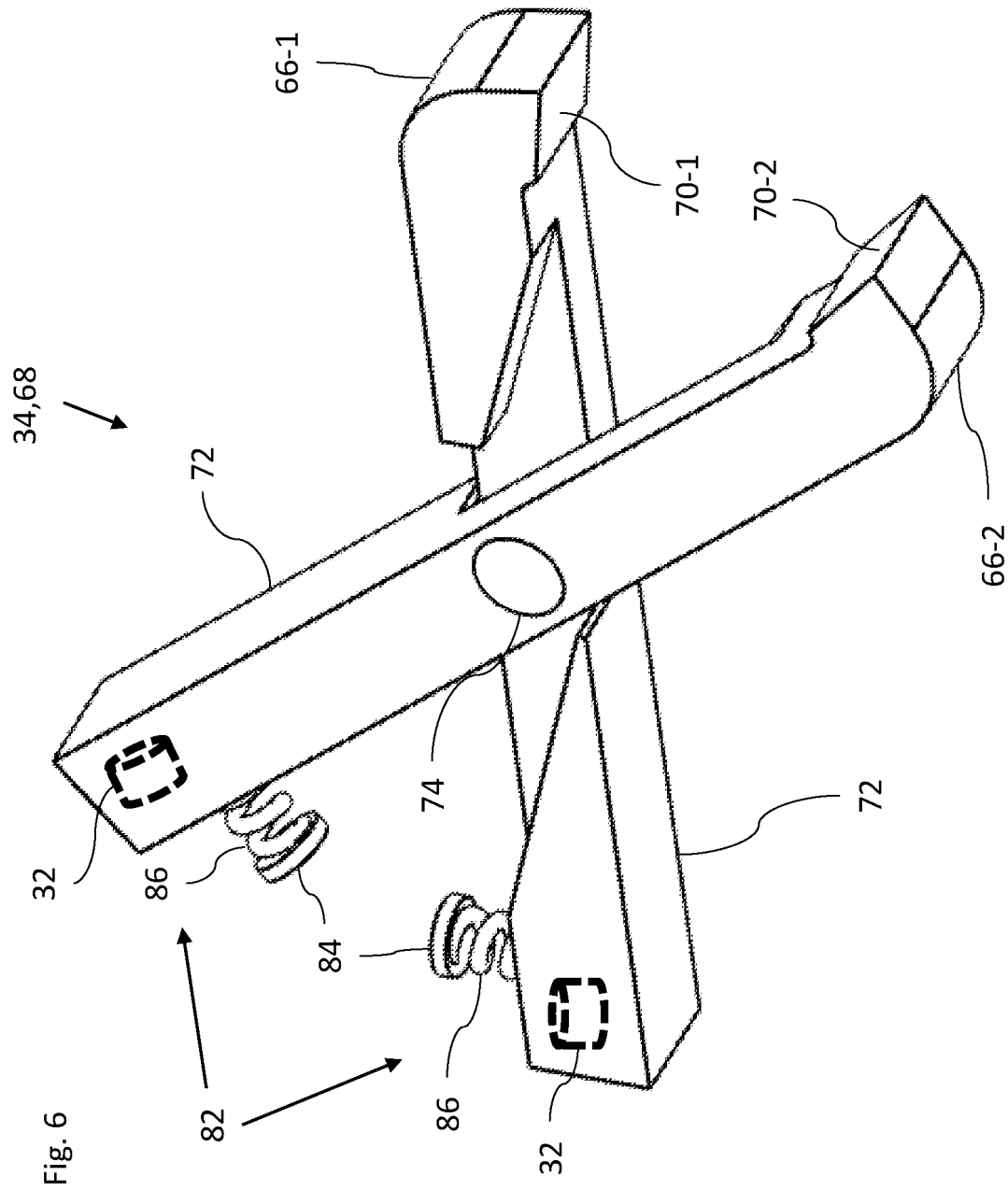

Reference is now made to FIGS. 3-6. FIG. 3 is a schematic illustration of the medical instrument 28 according to an embodiment of the present invention. FIGS. 4-6 are various schematic views of the distal end 34 of the medical instrument 28 of FIG. 3.

The medical instrument 28 includes a grasper head 68 having complementary grasping jaws 66 (individually labeled 66-1 and 66-2 in the drawings) and conducting surfaces 70 (individually labeled 70-1 and 70-2) disposed on respective distal portions of the grasping jaws 66, with the conducting surface 70-1 being disposed on the grasping jaw 66-1 and the conducting surface 70-2 being disposed on the grasping jaw 66-2. The grasping jaws 66 may optionally include one or more cutting edges (not shown). The conducting surfaces 70 may be formed from any suitable conducting material, for example, but not limited to, Platinum Iridium. The cutting edges may be formed from any suitable material for example, but not limited to, stainless steel. The dimensions of the grasper head 68 are in the order of millimeters.

The conducting surfaces 70 provide a region on the grasping jaws 66 through which to apply electrical current to tissue being grasped. The conducting surfaces 70 are electrically isolated from each other in the grasper head 68. This electrical isolation may be implemented by forming at least part of the grasper head 68 or at least part of the grasping jaws 66 from an insulating material, such as a biocompatible plastic. In some embodiments, the grasper head 68 and/or grasping jaws 66 may be formed from a conducting material which is coated with an insulating material, such as biocompatible plastic.

In some embodiments, the grasper head 68 comprises two elongated members 72, wherein each of the elongated members 72 includes one of the grasping jaws 66. The grasper head 68 also includes a pin 74 connecting the two elongated members 72 to allow angular motion between the grasping jaw 66-1 and the grasping jaw 66-2. The elongated members 72 may be at least partially formed from an insulating material so that the conducting surfaces 70 disposed on the grasping jaws 66 are electrically isolated from each other.

The medical instrument 28 also includes an actuator 76 configured to close the grasping jaws 66 so as to bring the conducting surface 70-1 and the conducting surface 70-2 into contact with a tissue of the body part of the living subject. In FIG. 3, the actuator 76 is shown including a pull handle 78 with a wire 80 which is connected to the proximal end of one of the elongated members 72 of the grasper head 68 so that pulling on the pull handle 78 closes the grasping jaws 66 together. The actuator 76 may comprise any suitable manual elements (for example, but not limited to, a handle with a scissor action connected to the grasper head 68 with a wire or rod) and/or automated elements (for example, but not limited to, using one or more motors and gears to control the opening and closing of the grasping jaws 66).

The grasper head 68 includes at least one position tracking transducer 32 configured to provide a position signal indicative of a position of the grasper head 68. In some embodiments, the grasper head 68 includes two position-tracking transducers 32, one position-tracking transducer 32 in each of the elongated members 72. The position-tracking transducer 32 are connected via wires 88 to the processing circuitry 38. Disposing one of the position-tracking transducers 32 in each of the elongated members 72 provides position data regarding each of the elongated members 72 and the position of each of the grasping jaws 66. The processing circuitry 38 is configured to compute a position of the grasper head 68 responsively to the position signal(s).

Each of the position-tracking transducers 32 may include 2 or 3 orthogonally placed coils or suitably placed electrodes. A representation of the medical instrument 28 including the grasper head 68 in a body part may be rendered to the display 56 based on the computed position. The physician 54 may then navigate the grasper head 68 within the body part according to the rendered representation of the medical instrument 28 including the grasper head 68.

The grasper head 68 includes a proximity sensor 82 configured to output one or more proximity signals responsive to a displacement between the grasping jaw 66-1 and the grasping jaw 66-2.

In some embodiments, the proximity sensor 82 includes two electrical contacts 84 disposed on the grasper head 68 on two opposing sides of the two elongated members 72. The electrical contacts 84 are connected via wires 88 to the processing circuitry 38. The electrical contacts 84 are configured to make mutual contact with each other when the displacement between the grasping jaw 66-1 and the grasping jaw 66-2 is less than a given threshold displacement. When the mutual contact is made, a circuit is completed resulting in a signal (i.e. the proximity signal) being sensed by the processing circuitry 38. The displacement may be measured as a distance or as an angular displacement. Respective ones of the electrical contacts 84 are connected to the elongated members 72 of the grasper head 68 via respective springs 86. The springs 86 allow the grasping jaws 66 to be closed even further than the given threshold displacement as well as to provide a restoring force to open the grasping jaws 66 when the actuator 76 releases closing of the grasping jaws 66.

In some embodiments, the proximity sensor 82 comprises two position tracking transducers 32 disposed in the grasper head 68. The position-tracking transducers 32 of the proximity sensor 82 are configured to provide proximity signals corresponding to respective position signals indicative of respective positions of the grasping jaw 66-1 and the grasping jaw 66-2.

The processing circuitry 38 is coupled to sense the displacement between the grasping jaw 66-1 and the grasping jaw 66-2 responsively to the proximity signal(s).

In embodiments where the proximity sensor 82 includes the electrical contacts 84, the processing circuitry 38 senses the displacement based on the two electrical contacts 84 making mutual contact thereby completing the electrical circuit resulting in the proximity signal flowing in the processing circuitry 38.

In embodiments where the proximity sensor 82 includes the position-tracking transducers 32, the processing circuitry 38 senses the displacement by computing the displacement between the grasping jaws responsively to the proximity signals (e.g., position signals) provided by the position-tracking transducers 32. The processing circuitry 38 is configured to compute the displacement between the grasping jaw 66-1 and the grasping jaw 66-2 responsively to the respective position signals. The displacement may be measured as a distance or as an angular displacement.

The processing circuitry 38 is configured to apply an electrical current between the conducting surface 70-1 and the conducting surface 70-2 of the grasping jaws 66 when the sensed displacement is less than the given threshold displacement. The processing circuitry 38 may apply the electrical current between the conducting surfaces 70 as a result of the two electrical contacts 84 making mutual contact and thereby closing a circuit resulting in the flow of the electrical current. Alternatively, the processing circuitry 38 may apply the electrical current in response to the computed displacement being less than the given threshold displacement. The electrical current may be any suitable electrical current, for example, but no limited to, a direct current (DC) or close to DC (e.g., a low frequency alternating current, such as up to 20 KHz). The power output used during coagulation may be any suitable value, for example, but not limited to, in the order of hundreds of watts.

The medical instrument 28 includes an irrigation tube 90 disposed therein and coupled to the irrigation pump 64. The irrigation pump 64 is configured to pump a fluid into the irrigation tube 90 to cool the tissue. The irrigation pump 64 may be activated in response to the electrical current flowing between the conducting surfaces 70.

Figure 7:
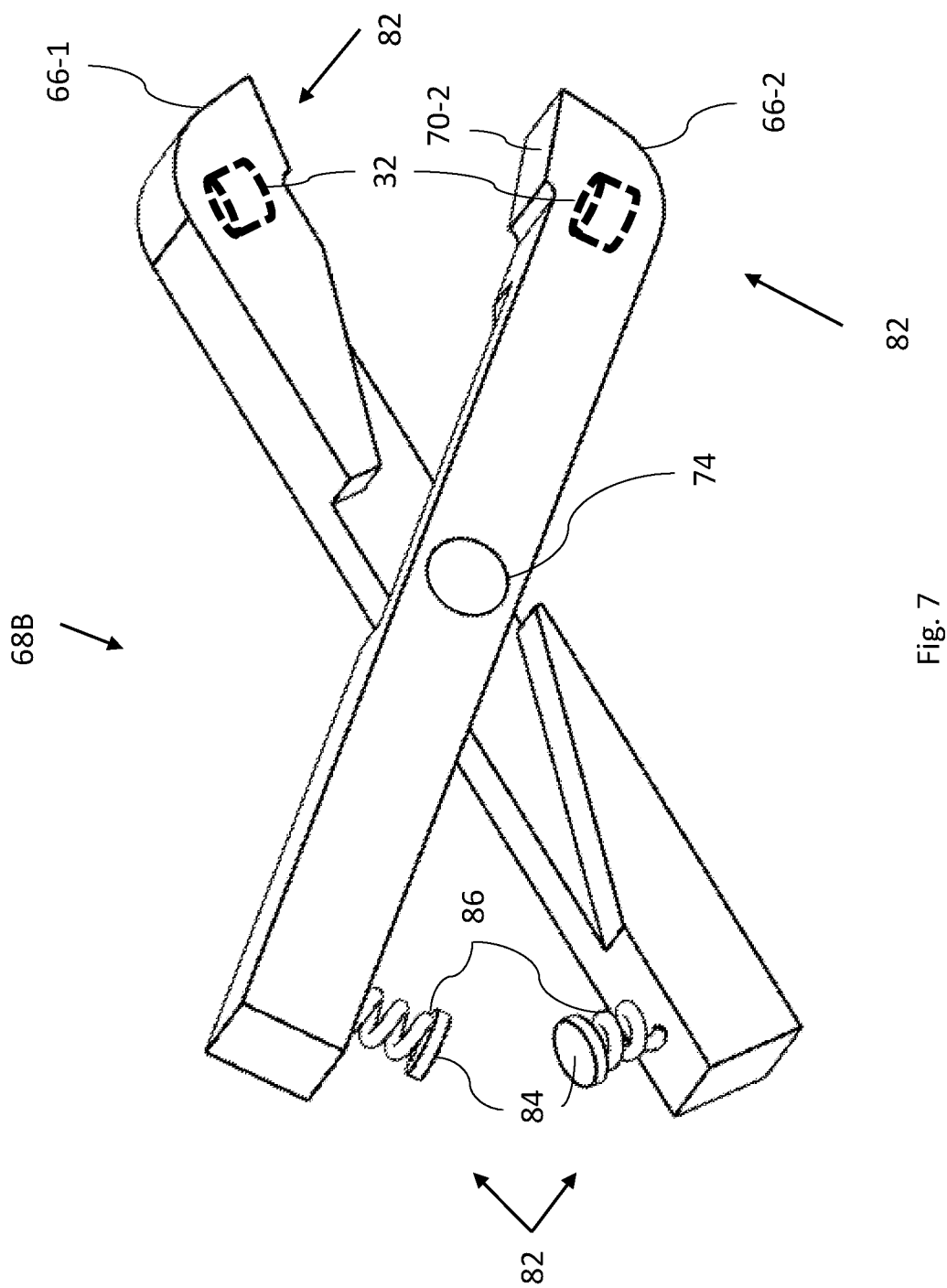
FIG. 7 is a schematic illustration of a grasper head according to a first alternative embodiment of the present invention.

Reference is now made to FIG. 7, which is a schematic illustration of a grasper head 68B according to a first alternative embodiment of the present invention. The grasper head 68B is substantially the same as the grasper head 68 of FIGS. 3-6 except that the position-tracking transducers 32 are disposed in the distal portion of the grasper head 68B adjacent to the conducting surfaces 70 of the grasping jaws 66.

Figure 8:
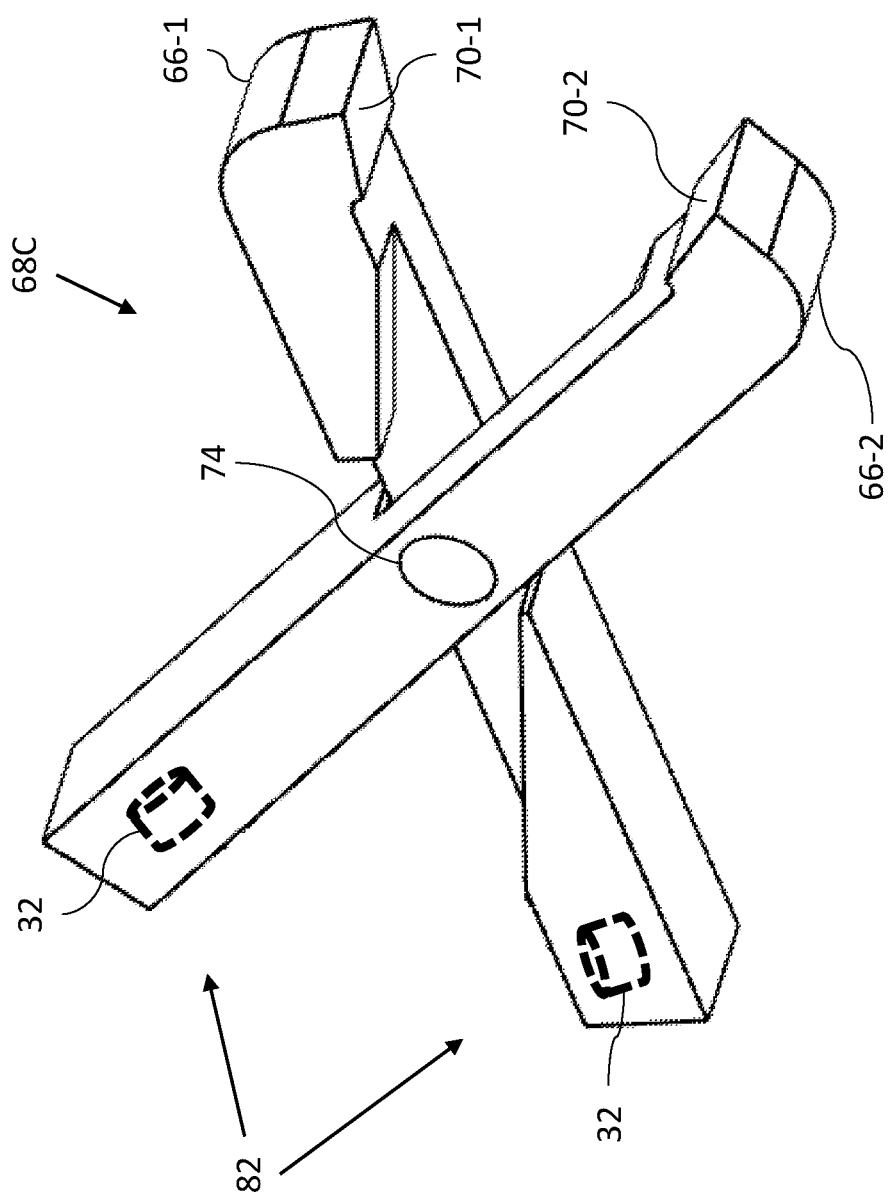
FIG. 8 is a schematic illustration of a grasper head according to a second alternative embodiment of the present invention.

Reference is now made to FIG. 8, which is a schematic illustration of a grasper head 68C according to a second alternative embodiment of the present invention. The grasper head 68C is substantially the same as the grasper head 68 of FIGS. 3-6 except that the grasper head 68C does not include the electrical contacts 84 or the springs 86. In the embodiment of FIG. 8, the displacement of the grasping jaws 66 is computed based on the position signals provided by the position-tracking transducers 32.

Reference is now made to FIG. 9, which is a flowchart 92 including exemplary steps in a method of operation of the system 20 of FIG. 1. Reference is also made to FIG. 3. It should be noted that the order of the steps presented below is exemplary and that the steps may be performed in any suitable order. In some embodiments, not all of the steps described below are performed. In some embodiments, one or more of the steps may be replaced by any suitable step or steps.

The actuator 76 is configured to close (block 94) the grasping jaws 66 so as to bring the conducting surfaces 70-1, 70-2 into contact with the tissue of the body part of the living subject.

The proximity sensor 82 is configured to output (block 96) at least one proximity signal responsive to a displacement between the grasping jaws 66.

When the proximity sensor 82 comprises the two electrical contacts 84 disposed on the elongated members 72 of the grasper head 68, the electrical contacts 84 are configured to make mutual contact with each other when the displacement between the grasping jaws 66 is less than the given threshold displacement. When the electrical contacts 84 make mutual contact, a circuit is completed resulting in a signal (i.e. the proximity signal) being sensed by the processing circuitry 38.

When the proximity sensor 82 includes the position-tracking transducers 32 disposed in the elongated members 72 of the grasper head 68, the proximity signals correspond to position signals provided by the position-tracking transducers 32.

The processing circuitry 38 is coupled to sense (block 98) the displacement between the grasping jaws 66 responsively to the proximity signal(s).

As mentioned previously, when the proximity sensor 82 comprises the two electrical contacts 84, when the electrical contacts 84 make mutual contact, a circuit is completed resulting in a signal (i.e. the proximity signal) being sensed by the processing circuitry 38.

When the proximity sensor 82 includes the position-tracking transducers 32, the displacement between the grasping jaws 66 is sensed by the processing circuitry 38 performing computations based on the provided position signals, as will now be described in more detail below. The processing circuitry 38 is configured to compute the displacement between the grasping jaws 66 responsively to the respective position signals.

The processing circuitry 38 is configured to apply (block 100) an electrical current between the conducting surfaces 70 of the grasping jaws 66 when the sensed displacement is less than the given threshold displacement.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and subcombinations of the various features described hereinabove, as well as variations and modifications thereof which would occur to persons skilled in the art upon reading the foregoing description and which are not disclosed in the prior art.

What is claimed is:
1. A medical system, comprising:
    (a) a medical instrument including:
        (i) a grasper head comprising:
            (A) first and second grasping jaws; and
            (B) first and second conducting surfaces disposed on respective distal portions of the first and second grasping jaws, the first and second conducting surfaces being electrically isolated from each other in the grasper head;
        (ii) an actuator configured to actuate the grasping jaws from an open state to a closed state so as to bring the first and second conducting surfaces into contact with a tissue of an anatomical structure of a patient; and
        (iii) a proximity sensor configured to output at least one proximity signal responsive to a displacement between the first and second grasping jaws, wherein the proximity sensor comprises two electrical contacts disposed on the grasper head and configured to make mutual contact with each other when the displacement between the first and second grasping jaws is less than a given threshold displacement, wherein respective ones of the electrical contacts are connected to the grasper head via respective springs configured to urge the grasping jaws from the closed state toward the open state; and
    (b) processing circuitry configured to:
        (i) sense the displacement between the first and second grasping jaws responsively to the at least one proximity signal, and
        (ii) apply an electrical current between the first and second conducting surfaces of the grasping jaws when the sensed displacement is less than the given threshold displacement, wherein each of the electrical contacts is electrically connected to the processing circuitry independently of the other of the electrical contacts.

2. The system according to claim 1, wherein the grasper head comprises at least one position tracking transducer configured to provide a position signal indicative of a position of the grasper head, and the processing circuitry being configured to compute a position of the grasper head responsively to the position signal.

3. The system according to claim 2, wherein the at least one position tracking transducer is configured to provide the position signal in response to exposure of the at least one position tracking transducer to an alternating magnetic field.

4. The system according to claim 3, wherein the at least one position tracking transducer includes at least one coil.

5. The system according to claim 1, wherein the proximity sensor further comprises two position tracking transducers disposed in the grasper head and configured to provide respective position signals, comprised in the at least one proximity signal, indicative of respective positions of the first and second grasping jaws, and the processing circuitry being configured to compute the displacement between the first and second grasping jaws responsively to the respective position signals.

6. The system according to claim 5, wherein each of the two position tracking transducers is configured to provide the respective position signal in response to exposure of the respective position tracking transducer to an alternating magnetic field.

7. The system according to claim 6, wherein each of the two position tracking transducers includes at least one coil.

8. The system according to claim 1, further comprising an irrigation pump, wherein the medical instrument includes an irrigation tube coupled to the irrigation pump, the irrigation pump being configured to pump a fluid into the irrigation tube to cool the tissue.

9. The system according to claim 8, wherein the irrigation pump is configured to pump the fluid when the sensed displacement is less than the given threshold displacement.

10. The system according to claim 1, wherein the grasper head comprises:
    (A) two elongated members including the first and second grasping jaws; and
    (B) a pin connecting the two elongated members to allow angular motion between the first and second grasping jaws.

11. The system according to claim 10, wherein the two electrical contacts are disposed on two opposing sides of the two elongated members.

12. A medical method, comprising:
    (a) closing first and second grasping jaws of a grasper head of a medical instrument so as to bring first and second conducting surfaces disposed on respective distal portions of the first and second grasping jaws into contact with a tissue of an anatomical structure of a patient, the first and second conducting surfaces being electrically isolated from each other in the grasper head;
    (b) outputting at least one proximity signal responsive to a displacement between the first and second grasping jaws, the act of outputting at least one proximity signal comprising two electrical contacts making mutual contact with each other when the displacement between the first and second grasping jaws is less than a given threshold displacement, wherein respective ones of the electrical contacts are connected to the grasper head via respective springs, wherein the electrical contacts are electrically isolated from the first and second conducting surfaces;

(c) sensing the displacement between the first and second grasping jaws responsively to the at least one proximity signal;

(d) applying an electrical current between the first and second conducting surfaces of the grasping jaws when the sensed displacement is less than the given threshold displacement; and (e) urging the first and second grasping jaws open via the springs.

13. The method according to claim 12, further comprising:

(a) providing a position signal indicative of a position of the grasper head; and (b) computing a position of the grasper head responsively to the position signal.

14. The method according to claim 12, further comprising:

(a) two position tracking transducers disposed in the grasper head providing respective position signals, comprised in the at least one proximity signal, indicative of respective positions of the first and second grasping jaws; and (b) computing the displacement between the first and second grasping jaws responsively to the respective position signals.

15. The method according to claim 12, further comprising pumping a fluid into an irrigation tube of the medical instrument to cool the tissue.

16. A system, comprising:

(a) an apparatus including:

(i) a grasper head comprising:

(A) first and second elongate members including first and second jaws, respectively, wherein the first and second elongate members are pivotably coupled to each other via a pin, (B) first and second conductive surfaces disposed on the first and second jaws, respectively, wherein the first and second conductive surfaces are each distal of the pin, and (C) first and second electrical contacts coupled to the first and second elongate members via first and second resilient biasing members, respectively, wherein the first and second electrical contacts are each proximal of the pin, wherein the first and second electrical contacts are configured to be electrically coupled with each other in response to a displacement between the first and second conductive surfaces being less than a threshold displacement, and (ii) an actuator configured to pivot the first and second elongate members relative to each other from an open state to a closed state for engaging each of the first and second conductive surfaces with a tissue of an anatomical structure of a patient;

(b) a controller configured to initiate application of an electrical current between the first and second conductive surfaces in response to the first and second electrical contacts being electrically coupled with each other;

(c) a first wire extending between the first elongate member and the controller, wherein the first electrical contact is electrically connected to the controller via the first wire; and (d) a second wire extending between the second elongate member and the controller, wherein the second electrical contact is electrically connected to the controller via the second wire.

17. The system according to claim 16, wherein the first and second elongate members include first and second exterior surfaces, respectively, wherein the first and second resilient biasing members extend from the first and second exterior surfaces to the first and second electrical contacts, respectively, such that the first and second resilient biasing members maintain the first and second electrical contacts external to the first and second exterior surfaces, respectively.

18. The system according to claim 16, wherein the first and second resilient biasing members are configured to urge the first and second elongate members from the closed state toward the open state.

19. The system according to claim 16, wherein the first and second resilient biasing members include first and second springs, respectively.

20. The system according to claim 19, wherein the first and second springs includes first and second coil springs, respectively.

* * * * *